(12) United States Patent
Chandra et al.

(10) Patent No.: US 7,790,149 B2
(45) Date of Patent: Sep. 7, 2010

(54) HAIR TREATMENT COMPOSITIONS

(75) Inventors: Lalitesh Chandra, Wirral (GB); Janet Cotterall, Wirral (GB); Laxmikant Tiwari, Eastleigh (GB)

(73) Assignee: Conopco, Inc., Englewood Cliffs, NJ (US)

( * ) Notice: Subject to any disclaimer, the term of this patent is extended or adjusted under 35 U.S.C. 154(b) by 1228 days.

(21) Appl. No.: 10/569,331

(22) PCT Filed: Jul. 23, 2004

(86) PCT No.: PCT/EP2004/008285

§ 371 (c)(1), (2), (4) Date: Feb. 21, 2006

(87) PCT Pub. No.: WO2005/018587

PCT Pub. Date: Mar. 3, 2005

(65) Prior Publication Data

US 2007/0009461 A1    Jan. 11, 2007

(30) Foreign Application Priority Data

Aug. 26, 2003   (EP)   ................................... 03255284

(51) Int. Cl.
*A61Q 5/02*    (2006.01)

(52) U.S. Cl. .................................. 424/70.22; 424/70.1

(58) Field of Classification Search ....................... None
See application file for complete search history.

(56) References Cited

U.S. PATENT DOCUMENTS 3,715,429 A    2/1973    Tobin et al. ................... 424/71

FOREIGN PATENT DOCUMENTS

| WO | 92/07877 | 5/1992 |
| WO | 99/15135 | 4/1999 |
| WO | 03/026599 | 4/2003 |

OTHER PUBLICATIONS

European Search Report in an EP application EP 03 25 5284.

*Primary Examiner*—Jyothsna A Venkat
(74) *Attorney, Agent, or Firm*—Karen E. Klumas

(57) ABSTRACT

The invention provides a rinse off hair treatment composition comprising a salt. The composition is for lengthening and straightening hair.

6 Claims, No Drawings

HAIR TREATMENT COMPOSITIONS

FIELD OF THE INVENTION

The invention relates to hair treatment compositions. The compositions are particularly suitable for application to straighten hair and in particular to lengthen it.

BACKGROUND AND PRIOR ART

Long, straight hair is an attribute considered attractive by many people in differing communities around the world. Hair growth stimulants are said to lengthen hair and are disclosed in EP 0 897 712 and WO92/07877.

Salts of alkali metals are disclosed in styling formulations in WO 99/151315.

The present application discloses formulations for lengthening hair. Attributes associated with hair lengthening are lowering the volume of hair and re-alignment of hair. The invention has the further advantages that it prevents the hair frizzing and increasing in volume.

DESCRIPTION OF THE INVENTION

In a first aspect, the present invention provides a rinse off hair treatment composition comprising:
i) from 0.4 wt % to 19.5 wt % of a salt selected from the group consisting of alkali metal sulphate, ammonium sulphate, alkali metal thiocyanate, ammonium thiocyanate or mixtures thereof; and in which the composition has a pH from 3 to 9.5 at 25° C.

In instances where the composition is solid the pH of a 5% aqueous solid should be measured.

A further aspect of the invention is the use of alkali metal sulphate, ammonium sulphate, alkali metal thiocyanate, ammonium thiocyanate, alkali metal tartrate or ammonium tartrate or mixtures thereof for straightening and/or lengthening hair.

Also described is a method of lengthening and/or straightening hair and/or lowering the volume and/or re-aligning by applying to the hair a composition comprising a salt selected from the group consisting of alkali metal sulphate, ammonium sulphate, alkali metal thiocyanate, ammonium thiocyanate, alkali metal tartrate or ammonium tartrate and mixtures thereof.

DETAILED DESCRIPTION OF THE INVENTION

The present invention is based on the finding that the use of certain salts are particularly useful in lengthening hair. The salts used in the present invention are alkali metal sulphate, ammonium sulphate, alkali metal thiocyanate, ammonium thiocyanate or mixtures thereof.

Sodium salts are preferred.

Mixtures of the above mentioned salts are particularly advantageous, especially mixtures of two salts from the above lists. Particularly preferred are the following pairs of salts: sodium sulphate and sodium thiocyanate, sodium sulphate and sodium tartrate or sodium thiocyanate and sodium tartrate.

Sodium sulphate is advantageous either used alone or more especially used in combination with one other salt. Particularly advantageous is combination of sodium sulphate and sodium tartrate.

The rinse off hair treatment composition of the invention comprises from 0.4 to 19.5 wt % of the total formulation of the salt or combination of salts more preferably from 0.5 to 5 wt %, most preferably from 1 wt % to 3 wt % of the total formulation.

Preferably the level of any one salt does not exceed 5 wt. % of the total formulation.

In some cases it is preferable if the composition is substantially free of sodium chloride. By substantially free it is meant that the composition comprises less than 0.1 wt % of the total formulation.

Surfactants

Shampoo compositions preferably comprise one or more cleansing surfactants, which are cosmetically acceptable and suitable for topical application to the hair. Further surfactants may be present as emulsifiers.

Suitable cleansing surfactants, are selected from anionic, nonionic, amphoteric and zwitterionic surfactants, however nonionic and anionic, especially anionic surfactants are preferred. The cleansing surfactant may be the same surfactant as the emulsifier, or may be different.

Anionic Cleansing Surfactant

Shampoo compositions according to the invention will preferably comprise one or more anionic cleansing surfactants, which are cosmetically acceptable and suitable for topical application to the hair.

Examples of suitable anionic cleansing surfactants are the alkyl sulphates, alkyl ether sulphates, alkaryl sulphonates, alkanoyl isethionates, alkyl succinates, alkyl sulphosuccinates, N-alkyl sarcosinates, alkyl phosphates, alkyl ether phosphates, alkyl ether carboxylates, and alpha-olefin sulphonates, especially their sodium, magnesium, ammonium and mono-, di- and triethanolamine salts. The alkyl and acyl groups generally contain from 8 to 18 carbon atoms and may be unsaturated. The alkyl ether sulphates, alkyl ether phosphates and alkyl ether carboxylates may contain from 1 to 10 ethylene oxide or propylene oxide units per molecule.

Typical anionic cleansing surfactants for use in shampoo compositions of the invention include sodium oleyl sulpho succinate, ammonium lauryl sulphosuccinate, ammonium lauryl sulphate, sodium cocoyl isethionate, sodium lauryl isethionate and sodium N-lauryl sarcosinate. The most preferred anionic surfactants are sodium lauryl sulphate, sodium lauryl ether sulphate(n)EO, (where n ranges from 1 to 3), ammonium lauryl sulphate and ammonium lauryl ether sulphate(n)EO, (where n ranges from 1 to 3).

The total amount of anionic cleansing surfactant in shampoo compositions of the invention is generally from 5 to 30, preferably from 6 to 20, more preferably from 8 to 16 wt %.

Co-Surfactant

The shampoo composition can optionally include co-surfactants, preferably an amphoteric or zwitterionic surfactant, which can be included in an amount ranging from 0 to about 8, preferably from 1 to 4 wt %.

Examples of amphoteric and zwitterionic surfactants include, alkyl betaines, alkyl amidopropyl betaines, alkyl sulphobetaines (sultaines), alkyl glycinates, alkyl carboxyglycinates, alkyl amphopropionates, alkylamphoglycinates, alkyl amidopropyl hydroxysultaines, acyl taurates and acyl glutamates, wherein the alkyl and acyl groups have from 8 to 19 carbon atoms. Typical amphoteric and zwitterionic surfactants for use in shampoos of the invention include lauryl amine oxide, cocodimethyl sulphopropyl betaine and preferably lauryl betaine, cocamidopropyl betaine and sodium cocamphopropionate.

Another preferred co-surfactant is a nonionic surfactant, which can be included in an amount ranging from 0 to 8, preferably from 2 to 5 wt %.

For example, representative nonionic surfactants that can be included in shampoo compositions of the invention include condensation products of aliphatic ($C_8$-$C_{18}$) primary or secondary linear or branched chain alcohols or phenols with alkylene oxides, usually ethylene oxide and generally having from 6 to 30 ethylene oxide groups.

Further nonionic surfactants which can be included in shampoo compositions of the invention are the alkyl polyglycosides (APGs). Typically, the APG is one which comprises an alkyl group connected (optionally via a bridging group) to a block of one or more glycosyl groups. Preferred APGs are defined by the following formula:

$$RO—(G)_n$$

wherein R is a branched or straight chain $C_5$ to $C_{20}$ alkyl or alkenyl group, G is a saccharide group and n is from 1 to 10.

Other sugar-derived nonionic surfactants which can be included in shampoo compositions of the invention include the $C_{10}$-$C_{18}$ N-alkyl ($C_1$-$C_6$) polyhydroxy fatty acid amides, such as the $C_{12}$-$C_{18}$ N-methyl glucamides, as described for example in WO 92 06154 and U.S. Pat. No. 5,194,639, and the N-alkoxy polyhydroxy fatty acid amides, such as $C_{10}$-$C_{18}$ N-(3-methoxypropyl) glucamide.

The shampoo composition can also optionally include one or more cationic co-surfactants included in an amount ranging from 0.01 to 10, more preferably from 0.05 to 5, most preferably from 0.05 to 2 wt %. Useful cationic surfactants are described hereinbelow in relation to conditioner compositions. It is preferable if the cationic co-surfactant is not present.

The total amount of surfactant (including any co-surfactant, and/or any emulsifier) in shampoo compositions of the invention is preferably greater than 0.5 wt %, more preferably 1 wt % or greater of the total composition, generally from 5 to 50, preferably from 5 to 30, more preferably from 10 to 25 wt %.

Cationic Polymer

A cationic polymer is a preferred ingredient in shampoo compositions of the invention, for enhancing conditioning performance of the shampoo.

Suitable cationic nitrogen polymers are described in the CTFA Cosmetic Ingredient Directory, 3rd edition The cationic conditioning polymer will generally be present in compositions of the invention at levels of from 0.01 to 5, preferably from 0.05 to 1, more preferably from 0.08 to 0.5 wt %.

Conditioning Surfactant

Although not a preferred form, the composition of the invention may be a conditioner. Conditioner compositions usually comprise one or more conditioning surfactants, which are cosmetically acceptable and suitable for topical application to the hair.

Suitable conditioning surfactants are selected from cationic surfactants, used singly or in admixture.

Cationic surfactants useful in compositions of the invention contain amino or quaternary ammonium hydrophilic moieties, which are positively charged when, dissolved in the aqueous composition of the present invention.

The most preferred cationic surfactants for conditioner compositions of the present invention are monoalkyl quaternary ammonium compounds in which the alkyl chain length is C16 to C22.

In the conditioners of the invention, the level of cationic surfactant is preferably from 0.01 to 10, more preferably 0.05 to 5, most preferably 0.1 to 2 wt % of the total composition.

Fatty Materials

Conditioner compositions of the invention preferably additionally comprise fatty materials. By "fatty material" is meant a fatty alcohol, an alkoxylated fatty alcohol, a fatty acid or a mixture thereof.

(Or propoxylated) fatty alcohols having from about 12 to about 18 carbon atoms in the alkyl chain can be used in place of, or in addition to, the fatty alcohols themselves. Suitable examples include ethylene glycol cetyl ether, polyoxyethylene (2) stearyl ether, polyoxyethylene (4) cetyl ether, and mixtures thereof.

The level of fatty alcohol material in conditioners of the invention is suitably from 0.01 to 15, preferably from 0.1 to 10, and more preferably from 0.1 to 5 wt %. The weight ratio of cationic surfactant to fatty alcohol is suitably from 10:1, to 1:10, preferably from 4:1 to 1:8, optimally from 1:1 to 1:7, for example 1:3.

Further Optional Ingredients

Suspending Agents

In a preferred embodiment, the rinse off hair treatment composition, especially if it is a shampoo composition, further comprises from 0.1 to 5 wt % of a suspending agent.

Silicone Conditioning Agents

The compositions of the invention can contain, emulsified droplets of a silicone-conditioning agent, for enhancing conditioning performance.

Suitable silicones include polydiorganosiloxanes, in particular polydimethylsiloxanes which have the CTFA designation dimethicone. Also suitable for use compositions of the invention (particularly shampoos and conditioners) are polydimethyl siloxanes having hydroxyl end groups, which have the CTFA designation dimethiconol. Also suitable for use in compositions of the invention are silicone gums having a slight degree of cross-linking, as are described for example in WO 96/31188.

A further preferred class of silicones for inclusion in shampoos and conditioners of the invention are amino function.

The total amount of silicone is preferably from 0.01 to 10% wt of the total composition more preferably from 0.3 to 5, most preferably 0.5 to 3 wt % is a suitable level.

(ii) Non-Silicone Oily Conditioning Components

Compositions according to the present invention may also comprise a dispersed, non-volatile, water-insoluble oily conditioning agent.

By "insoluble" is meant that the material is not soluble in water (distilled or equivalent) at a concentration of 0.1% (w/w), at 25° C.

Suitable oily or fatty materials are selected from hydrocarbon oils, fatty esters and mixtures thereof.

Adjuvants

The compositions of the present invention may also contain adjuvants suitable for hair care. Generally such ingredients are included individually at a level of up to 2, preferably up to 1 wt % of the total composition.

Suitable hair care adjuvants, include amino acids, sugars and ceramides.

The invention will now be further illustrated by the following, non-limiting Examples.

Examples of the invention are illustrated by a number, Comparative Examples are illustrated by a letter. All percentages quoted are by weight based on total weight unless otherwise stated.

Product Form

The rinse off hair treatment compositions according to the invention may suitably be any product form suitable for application to the hair. In the context of the present invention the term rinse off means that the product is applied to the hair and is not left on the hair for a period greater than half an hour without a rising procedure taking place. In most cases the product is applied to the hair and after the treatment has taken place, immediately rinsed off The invention is particularly advantageous if it is formulated as a shampoo.

The product is preferably formulated in an aqueous base and has a pH from 3 to 9.5, more preferably from 3.5 to 7.

EXAMPLES

| Raw Materials | INCI Names | Example A | Example 1 |
|---|---|---|---|
| SLES 70% | Sodium Laureth Sulfate | 15.426 | 15.426 |
| CAPB | Cocamidopropylbetaine | 4.797 | 4.797 |
| Jaguar C13S | Guar Hydroxypropyltrimonium chloride | 0.09 | 0.09 |
| Betafine BP20 | Betaine | 0.9 | 0.9 |
| Silicone 1785 | Dimethiconol, TEA - Dodecylbenzenesulfonate | 0.747 | 0.747 |
| Silicone 949 | Amodimethicone and Cetrimonium Chloride and Trideceth-12 | 1.449 | 1.449 |
| Glydant LTD | DMDM Hydantoin | 0.36 | 0.36 |
| Carbopol 980 | Carbomer | 0.36 | 0.36 |
| Citric Acid | citric acid | 0.09 | 0.09 |
| | sodium Hydroxide | 0.216 | 0.216 |
| | sodium chloride | 1.53 | 1.53 |
| | Sodium tartrate | | 2.00 |
| | Sodium sulphate | | 2.00 |
| | Polypropylene glycol | | 0.10 |
| | Water and minors | to 100 | to 100 |
| pH | | 6-6.5 | 6-6.5 |
| Visco | | 6000-8000 cps | 6000-8000 cps |

The Examples were applied to consumers hair, one Example being placed on one half of the head, the other Example being placed on the other half. The hair was washed twice in this way, and then one side compared with the other half while wet. A total of 31 panellists were assessed by an expert assessor.

Salon Results:

| Attribute | % Panellists for Example 1 | Statistical Significance; Level of Confidence |
|---|---|---|
| Most Lengthened appearance | 64.52 | 89.65% |
| Most Looseness of curl | 70.97 | 98.23% |
| Most Conditioned feel | 74.19 | 99.41% |
| Easiest to Straighten | 64.52 | 89.65% |

Thus it is demonstrated that Example 1 has better hair lengthening attributes and better conditioning than comparative Example A.

The invention claimed is:

1. A rinse off hair treatment composition comprising:
   i) from 0.4 wt % to 19.5 wt % of a salt pair selected from:
      sodium sulphate and sodium thiocyanate,
      sodium sulphate and sodium tartrate, and
      sodium thiocyanate and sodium tartrate; and
   ii) from 6 to 20 wt. % of anionic surfactant:
   in which the composition is in the form of a shampoo that has a pH from 3 to 9.5 at 25° C.

2. A rinse off hair treatment composition according to claim 1 further comprising co-surfactant.

3. A rinse off hair treatment composition according to claim 2 wherein the co-surfactant is present in the composition in an amount of from 1 to 4 wt. %.

4. A rinse off hair treatment composition according to claim 1 which comprises of a combination of sodium sulphate and sodium tartrate.

5. A rinse off hair treatment composition according to claim 1 which comprises less than 0.1 wt % of the total formulation of sodium chloride.

6. A rinse off hair treatment composition according to claim 1 which comprises an aqueous base.

* * * * *